United States Patent
Lee (10) Patent No.: US 8,539,823 B2
(45) Date of Patent: Sep. 24, 2013

(54) MICROFLUIDIC DEVICE AND METHOD OF LOADING SAMPLE INTO THE MICROFLUIDIC DEVICE

(75) Inventor: Beom-seok Lee, Hwaseong-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 644 days.

(21) Appl. No.: 12/546,302

(22) Filed: Aug. 24, 2009

(65) Prior Publication Data

US 2010/0050751 A1    Mar. 4, 2010

(30) Foreign Application Priority Data

Sep. 2, 2008    (KR) .................. 10-2008-0086290

(51) Int. Cl.
| | |
|---|---|
| G01N 1/00 | (2006.01) |
| F16K 3/00 | (2006.01) |
| B01L 3/00 | (2006.01) |
| F04B 19/00 | (2006.01) |
| F15C 1/00 | (2006.01) |
| G01N 9/30 | (2006.01) |
| G01N 33/00 | (2006.01) |
| F15C 1/06 | (2006.01) |

(52) U.S. Cl.
USPC ............ 73/64.56; 73/863; 137/803; 137/833; 422/68.1; 422/502; 422/504; 422/505; 422/506; 422/507; 422/72; 422/547

(58) Field of Classification Search
USPC ....................................................... 73/64.56
See application file for complete search history.

(56) References Cited

U.S. PATENT DOCUMENTS

| | | | | |
|---|---|---|---|---|
| 5,061,381 | A | * | 10/1991 | Burd .............................. 210/789 |
| 5,173,262 | A | * | 12/1992 | Burtis et al. .................... 422/72 |
| 5,591,643 | A | * | 1/1997 | Schembri ........................ 436/45 |
| 6,063,589 | A | * | 5/2000 | Kellogg et al. ................. 435/24 |
| 6,803,019 | B1 | * | 10/2004 | Bjornson et al. ............... 422/66 |
| 6,900,021 | B1 | * | 5/2005 | Harrison et al. ............. 435/7.21 |
| 2003/0019522 | A1 | * | 1/2003 | Parunak ..................... 137/251.1 |
| 2004/0079424 | A1 | * | 4/2004 | Takeda et al. ............. 137/624.13 |
| 2004/0241049 | A1 | * | 12/2004 | Carvalho ....................... 422/100 |
| 2008/0171400 | A1 | * | 7/2008 | Cho et al. ...................... 436/526 |
| 2009/0220948 | A1 | * | 9/2009 | Oviso et al. ....................... 435/6 |
| 2009/0238724 | A1 | * | 9/2009 | Yamamoto et al. .......... 422/68.1 |
| 2009/0317896 | A1 | * | 12/2009 | Yoo ............................. 435/287.1 |

FOREIGN PATENT DOCUMENTS

| | | |
|---|---|---|
| JP | 2005-177754 A | 7/2005 |
| JP | 2008-185517 A | 8/2008 |

OTHER PUBLICATIONS

Communication dated Mar. 27, 2013, issued by the Korean Intellectual Property Office in counterpart Korean Application No. 10-2008-0086290.

* cited by examiner

*Primary Examiner* — Brian J Sines
*Assistant Examiner* — Jennifer Wecker
(74) *Attorney, Agent, or Firm* — Sughrue Mion, PLLC (57) ABSTRACT

Provided is a microfluidic device. The microfluidic device includes a sample chamber in which a sample is accommodated. The sample chamber includes: an introduction portion including a loading hole through which the sample is loaded; an accommodation portion including a discharge hole; and a neck portion forming a boundary between the introduction portion and the accommodation portion. The neck portion provides a capillary pressure for controlling flow of the sample between the introduction portion and the accommodation portion.

20 Claims, 5 Drawing Sheets

MICROFLUIDIC DEVICE AND METHOD OF LOADING SAMPLE INTO THE MICROFLUIDIC DEVICE

CROSS-REFERENCE TO RELATED APPLICATION

This application claims the benefit of Korean Patent Application No. 10-2008-0086290, filed on Sep. 2, 2008, in the Korean Intellectual Property Office, the disclosure of which is incorporated herein in their entirety by reference.

BACKGROUND

1. Field

One or more embodiments relate to a microfluidic device having a microfluidic structure and a method of loading a sample into the microfluidic device.

2. Description of the Related Art

Various methods of analyzing samples have been developed in a variety of application fields, such as environmental monitoring, food inspection, medical diagnostics, etc. Related inspection methods require a lot of manual work and various equipment. In order to perform inspection by using a predetermined protocol, a skilled practitioner may manually perform various operations, such as loading of samples several times, mixture, separation and movement, reaction, centrifugal separation, etc. These manual operations lead to errors in inspection results.

In order to quickly perform inspection, a skilled medical technician is necessary. However, it is difficult for even a skilled medical technician to perform some inspections simultaneously. Nevertheless, fast inspection results are very important for fast emergency measures when diagnosing emergency patients. Thus, an apparatus which simultaneously, quickly, and accurately performs required pathological inspections is required.

Even in related medical pathological inspections, large and expensive automation equipment is used, and a relatively large amount of inspection materials such as blood, etc. is required. In addition, it takes a long time to perform medical pathological inspections. After inspection materials are taken from a patient, the patient receives the inspection result 2-14 days later.

In order to overcome these problems, minimized and automated equipment which quickly analyzes inspection materials taken from one or more patients if necessary has been developed. As an example thereof, when blood is loaded into a disc-shaped microfluidic device and the microfluidic device is rotated, serum separation occurs due to a centrifugal force. Separated serum is mixed with a predetermined amount of dilution buffer and is moved to a plurality of reaction chambers within the disc-shaped microfluidic device. Different reagents are loaded into the plurality of reaction chambers in advance according to items of blood inspection and react with the serum so that a predetermined color is represented. Blood analysis can be performed by detecting variations in the color.

SUMMARY

One or more embodiments include a microfluidic device which does not allow a sample treated in a sample chamber to leak through a loading hole.

One or more embodiments include a microfluidic device which checks whether a fixed amount of sample is loaded into a sample chamber and a method of loading a sample.

To achieve the above and/or other aspects, one or more embodiments may include a microfluidic device including a sample chamber in which a sample is accommodated, wherein the sample chamber includes: an introduction portion including a loading hole through which the sample is loaded; an accommodation portion including a discharge hole; and a neck portion forming a boundary between the introduction portion and the accommodation portion and forming a capillary pressure for controlling flow of the sample between the introduction portion and the accommodation portion.

The microfluidic device may further include an analysis unit which receives the sample accommodated in the sample chamber and analyzes the sample.

A bottom of the introduction portion may be inclined upward to the neck portion from the loading hole.

The microfluidic device may further include a distance maintaining portion maintaining a distance between a front end part of a sample loader inserted in the loading hole and a bottom of the introduction portion, wherein the distance maintaining portion is disposed in the introduction portion.

The microfluidic device may further include a backward flow prevention portion disposed in the accommodation portion, wherein the backward flow prevention portion protrudes from a bottom of the accommodation portion.

The microfluidic device may include at least a backward flow prevention portion disposed in a direction that crosses a direction of a sample flowing into the discharge hole.

An end part of the backward flow prevention portions directing toward the neck portion may be inclined upward toward the discharge hole.

The analysis unit may include: a sample measuring portion connected to the sample chamber and measuring the sample; and a sample detection chamber which is connected to the sample measuring portion and in which a sample exceeding a capacity of the sample measuring portion is accommodated.

The analysis unit may further include a surplus sample chamber which is connected to the sample detection chamber and in which a sample exceeding a capacity of the sample detection chamber is accommodated.

The sample measuring portion may separate the sample into a supernatant and a sedimentation material due to a centrifugal force.

The analysis unit may include: a dilution chamber in which a dilution buffer is accommodated, which is connected to the sample measuring portion and to which the supernatant is supplied; and a detection chamber in which a reagent is accommodated and to which a mixture of the supernatant and the dilution buffer is supplied from the dilution chamber.

The analysis unit may further include a measuring chamber positioned between the dilution chamber and the sample measuring portion and accommodating a fixed amount of the supernatant.

The analysis unit may further include a valve disposed in channels connecting the sample measuring portion, the measuring chamber, the dilution chamber, and the detection chamber, to control a flow of a fluid.

To achieve the above and/or other aspects, one or more embodiments may include a microfluidic device including: an analysis unit analyzing a material included in a sample, wherein the analysis unit includes: a sample measuring portion measuring the sample; and a sample detection chamber which is connected to the sample measuring portion and in which a sample exceeding a capacity of the sample measuring portion is accommodated.

To achieve the above and/or other aspects, one or more embodiments may include a method of loading a sample, the method including: loading a sample into a sample chamber of a microfluidic device; rotating the microfluidic device and moving the sample to a sample measuring portion due to a centrifugal force; and checking whether a sample exceeding a capacity of the sample measuring portion is accommodated in a sample detection chamber connected to the sample measuring portion.

The method may further include, when a sample is not detected in the sample detection chamber, loading the sample into the sample chamber.

The checking of whether a sample exceeding a capacity of the sample measuring portion is accommodated in the sample detection chamber may include irradiating light on the sample detection chamber and detecting light absorption of the sample detection chamber by using a photodetector.

The method may further include, before the loading of the sample into the microfluidic device, checking whether a sample exists in the sample detection chamber, and when it is checked that a sample exists in the sample detection chamber, replacing the microfluidic device with a new microfluidic device.

BRIEF DESCRIPTION OF THE DRAWINGS

These and/or other aspects will become apparent and more readily appreciated from the following description of the embodiments, taken in conjunction with the accompanying drawings of which.

DETAILED DESCRIPTION

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description.

Figure 1:
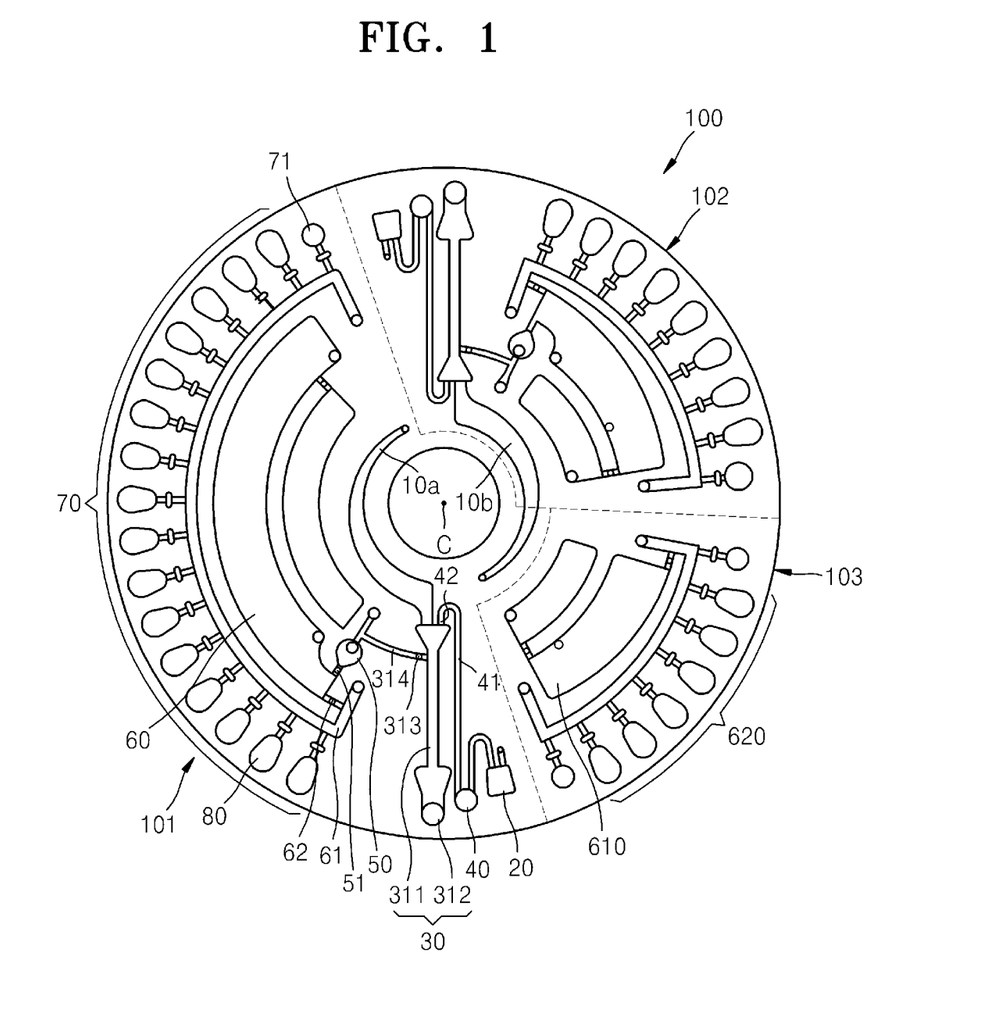
FIG. 1 illustrates a microfluidic device according to an embodiment.

FIG. 1 illustrates a microfluidic device according to an embodiment. Referring to FIG. 1, the microfluidic device according to the present embodiment includes a rotatable (for example, a disc-shaped) platform 100 and microfluidic structures which provide a space in which fluid can be accommodated and a flow path through which fluid flows to the platform 100. The platform 100 may be rotated around the center C thereof. The microfluidic device may be mounted at a rotation driving portion (510 of FIG. 8) of an analyzing device that will be described later and may be rotated. In this case, within the microfluidic structures disposed within the platform 100, movement, centrifugal separation, and mixture of a sample is performed due to the effect of a centrifugal force caused by rotation of the platform 100.

Figure 2:
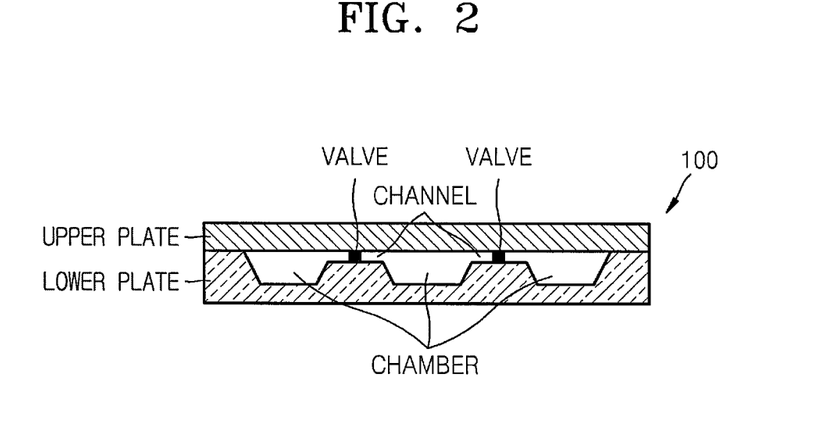
FIG. 2 is a cross-sectional view of a microfluidic device having a two-plate structure according to an embodiment.
Figure 3:
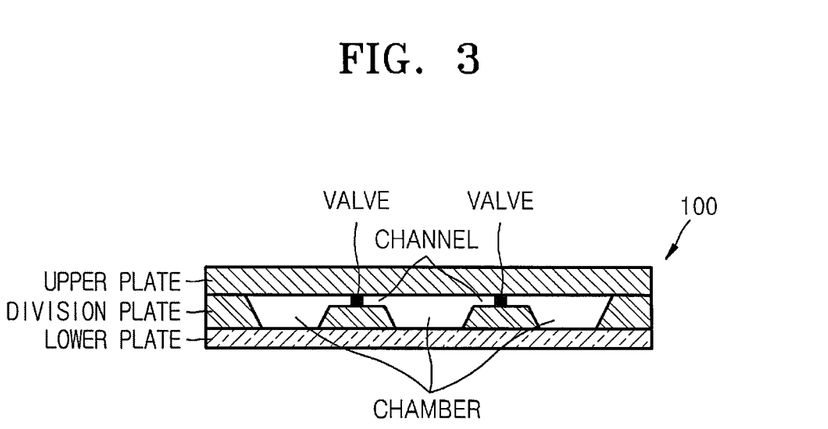
FIG. 3 is a cross-sectional view of a microfluidic device having a three-plate structure according to an embodiment.

The platform 100 may be formed of plastics, such as acryl, polydimethylsiloxane (PDMS), etc. which can be easily formed, and has a biologically non-volatile surface. However, one or more embodiments are not limited thereto, and the platform 100 may be formed of a material having chemical and biological stability, optical transparency, and mechanical processibility. The platform 100 may be formed of a plate having a plurality of layers. A space and a passage can be provided inside the platform 100 by forming intaglio structures corresponding to a chamber or channel, etc. at a surface which plates contact each other and by bonding the plates. The plates may be bonded to each other by using various methods, such as adhesion using an adhesive or double-sided adhesive tape, ultrasonic fusion, laser welding, etc. For example, the platform 100 may be a double-plated structure including an upper plate and a lower plate, as illustrated in FIG. 2. In addition, the platform 100 may include a division plate for defining a space in which a fluid is accommodated and a passage through which the fluid flows, the division plate being disposed between the lower and upper plates, as illustrated in FIG. 3. In addition, the platform 100 may have various shapes.

The microfluidic structures disposed within the platform 100 will now be described. For purposes of description, points on the platform 100 close to the center C of the platform 100 in a radial direction are referred to being on the inside, and points on the platform 100 far from the center C of the platform 100 in the radial direction are referred to being on the outside. Of a plurality of chambers disposed in the platform 100, sample chambers 10a and 10b are the nearest to the center C of the platform 100. Samples are accommodated in the sample chambers 10a and 10b.

As an example thereof, the microfluidic device according to the current embodiment includes two (first and second) analysis units 101 and 102 which are respectively connected to the sample chambers 10a and 10b. For example, Albumin (ALB), Alkaline Phosphatase (ALP), Amylase (AMY), Urea Nitrogen (BUN), calcium (Ca++), Total Cholesterol (CHOL), Chloide (Cl—), Creatinine (CRE), Glucose (GLU), High-Density Lipoprotein cholesterol (HDL), Potassium (K+), Lactate Dehydrogenase (LD), Sodium (Na+), Total Bilirubin (T-BIL), Total Protein (TP), Triglycerides (TRIG), and Uric Acid (UA) require a rate of dilution of serum: dilution buffer=1:100. In addition, alanine aminotransferase (ALT), aspartate aminotransferase (AST), Creatine Kinase (CK), Direct Bilirubin (D-BIL), and Gamma Glutamyl Transferase (GGT) require a rate of dilution of serum: dilution buffer=1:20. Thus, the first analysis unit 101 may be a unit for inspecting inspection items which require a rate of dilution of serum: dilution buffer=1:100, and the second analysis unit 102 may be a unit for inspecting inspection items which require a rate of dilution of serum: dilution buffer=1:20.

In this embodiment, the two analysis units 101 and 102 are used to inspect inspection items having different rates of dilution of a sample and a dilution buffer, and their configuration is the same. Thus, hereinafter, detailed configuration of the analysis unit 101 will be described. Also, the two analysis units 101 and 102 may be used to inspect inspection items having the same rate of dilution of a sample and a dilution buffer.

The sample chamber 10a is connected to a sample measuring portion 30 of the first analysis unit 101. The sample measuring portion 30 is used to accommodate a fixed amount of sample that is appropriate for inspection. Since a centrifugal force caused by rotation of the platform 100 is used to deliver the sample to the sample measuring portion 30 from the sample chamber 10a, the sample measuring portion 30 is positioned further away from the center C of the platform 100 than the sample chamber 10a. In addition, the sample measuring portion 30 may serve as a centrifugal separator which separates a sample (e.g., blood) into a supernatant and a sedimentation material by rotation of the platform 100. The sample measuring portion 30 for centrifugal separation may be constituted in various shapes, and an example thereof is illustrated in FIG. 1. The sample measuring portion 30 may include a supernatant collecting portion 311 having a channel shape extending to the outside from the sample chamber 10a and a sedimentation material collecting portion 312 which is positioned at the end of the supernatant collecting portion 311 and provides a space in which a sedimentation material having a larger specific gravity is collected. A sample distribution channel 314 which distributes the collected supernatant (e.g., serum when blood is used as a sample) to a next stage structure, is disposed at one side of the supernatant collecting portion 311. The sample distribution channel 314 is connected to the supernatant collecting portion 311 through a valve 313. A position in which the sample distribution channel 314 is connected to the supernatant collecting portion 311 may be changed according to the amount of a sample to be distributed. In other words, the amount of the sample to be distributed depends on the volume of a part of the supernatant collecting portion 311 that is close to the center C based on the valve 313. Strictly, when a measuring chamber 50 is further provided, as will be described later, the amount of the sample to be distributed depends on the capacity of the measuring chamber 50.

The valve 313 may be a microfluidic valve having various shapes. The valve 313 may be a valve that is passively opened when a predetermined pressure is applied to the valve, such as a capillary valve, or a valve that actively operates due to power or energy externally supplied when an operating signal is applied.

The valve 313 is a normally closed valve which closes the sample distribution channel 314 so that a fluid cannot flow before electromagnetic wave energy is absorbed.

The valve 313 may be formed of a thermoplastic resin, such as cyclic olefin copolymer (COC), polymethylmethacrylate (PMMA), polycarbonate (PC), polystyrene (PS), polyoxymethylene (POM), perfluoralkoxy (PFA), polyvinylchloride (PVC), polypropylene (PP), polyethylene terephthalate (PET), polyetheretherketone (PEEK), polyamide (PA), polysulfone (PSU), or polyvinylidene fluoride (PVDF).

In addition, the valve 313 may be formed of a phase change material which is in a solid state at room temperature. In this case, the phase change material in a melted state is loaded into the sample distribution channel 314 and is solidified to close the sample distribution channel 314. The phase change material may be a wax. In this case, the wax is heated, is melted, and is changed into a liquid state, and its volume expands. The wax may be a paraffin wax, a microcrystalline wax, a synthetic wax, a natural wax, or the like. The phase change material may be a gel or thermoplastic resin. The gel may be polyacrylamide, polyacrylates, polymethacrylates, polyvinylamides, or the like.

A plurality of micro heating particles, which absorb electromagnetic wave energy and dissipate heat, may be dispersed in the phase change material. The micro heating particles have a diameter of 1 nm to 100 μm so that they can freely pass through the sample distribution channel 314 having a depth of about 0.1 mm and a width of 1 mm. The temperature of the micro heating particles is rapidly increased and the micro heating particles dissipate heat when electromagnetic wave energy in the form of laser or the like is supplied thereto, and are uniformly dispersed in the phase change material. The micro heating particles may have a core containing a metal component and a hydrophobic surface structure so as to have these properties. For example, the micro heating particles may include a core formed of Fe and a molecular structure including a plurality of surfactants that are combined with Fe and encompass Fe. The micro heating particles may be maintained in a state dispersed in a carrier oil. The carrier oil may be hydrophobic so that the micro heating particles having the hydrophobic surface structure can be uniformly dispersed therein. The carrier oil in which the micro heating particles are dispersed is poured in the melted phase change material and is mixed therewith, and the mixed material is loaded into the sample distribution channel 314 and is solidified to close the sample distribution channel 314.

The micro heating particles are not limited to polymer particles as described above and may have the shape of quantum dots or magnetic beads. In addition, the micro heating particles may be formed of micro metal oxides, such as $Al_2O_3$, $TiO2$, $Ta_2O_3$, $Fe_2O_3$, $Fe_3O_4$ or $HfO_2$. Alternatively, the valve 313 may not include micro heating particles and may be formed of a phase change material without micro heating particles dispersed therein. At least a portion of the platform 100 is transparent so that electromagnetic waves transmitted from the outside of the platform 100 can be radiated to the valve 313.

The sample distribution channel 314 is connected to the measuring chamber 50 which accommodates the supernatant separated from the sample. The measuring chamber 50 is connected to the dilution chamber 60 through a valve 51. The valve 51 may be a microfluidic valve having the same shape as the above-described valve 313.

A sample detection chamber 40 is connected to the sample measuring portion 30. The sample detection chamber 40 is connected to the sample measuring portion 30 through a channel 41 so as to accommodate a surplus sample when a sample exceeding an amount appropriate for inspection flows into the sample measuring portion 30. In other words, a position of a connection portion 42 of the channel 41 and the sample measuring portion 30 is determined so that the capacity of the sample measuring portion 30 corresponding to the outside region is equal to or greater than the capacity of accommodating an amount of a sample appropriate for inspection. In the current embodiment, the connection portion 42 is positioned at the uppermost end of the sample measuring portion 30.

In addition, the microfluidic device according to the current embodiment may further include a surplus sample chamber 20 which accommodates a sample exceeding the capacity of the sample detection chamber 40.

The dilution chamber 60 is used to provide a sample dilution buffer in which a supernatant and a dilution buffer are mixed in a predetermined ratio. A predetermined amount of dilution buffer is accommodated in the dilution chamber 60 in consideration of the dilution rate of supernatant and dilution buffer, which are needed for inspection. The measuring chamber 50 is designed to have the capacity of accommodating a predetermined amount of sample in consideration of the dilution rate. A sample exceeding the capacity of the measuring chamber 50 cannot flow into the measuring chamber 50 provided the valve 51 is maintained in a closed state. As such, a fixed amount of supernatant can be provided to the dilution chamber 60. It would have been obvious to one of ordinary skill in the art that a position in which, as described above, the sample distribution channel 314 and the supernatant collecting portion 311 are connected, is precisely designed so that the sample distribution channel 314 and the dilution chamber 60 can be directly connected to each other without the measuring chamber 50.

Reaction chambers 70 are disposed outside the dilution chamber 60. The reaction chambers 70 are connected to the dilution chamber 60 through a distribution channel 61. Distribution of a sample dilution buffer through the distribution channel 61 can be controlled by a valve 62. The valve 62 may be a microfluidic valve having the same shape as the above-described valve 313.

Reagents that cause different types of reactions with the sample dilution buffer may be accommodated in the reaction chambers 70. The reagents may be loaded before the upper plate and the lower plate of the platform 100 are bonded to each other when the microfluidic device is manufactured. In addition, the reaction chambers 70 may be reaction chambers each having a vent and a loading hole as well as closed-type reaction chambers. If the reaction chambers 70 have a vent and a loading hole, the reagents may be loaded into the reaction chambers 70 before inspection. The reagents may be in a liquid state or lyophilized solid state.

For example, liquid reagents may be loaded into the reaction chambers 70 and may be simultaneously lyophilized by using a lyophilisation process before the upper plate and the lower plate of the platform 100 are bonded to each other when the microfluidic device is manufactured. After that, the upper plate and the lower plate are adhered to each other, thus providing a microfluidic device in which lyophilized reagents are accommodated. In addition, cartridges in which the lyophilized reagents are accommodated may be loaded into the reaction chambers 70. The lyophilized reagents may be reagents produced by adding a filler and a surfactant to liquid reagents and by lyophilizing them. The filler allows the lyophilized reagents to have a porous structure so that, when a sample dilution buffer in which a sample and a dilution buffer are mixed is provided into the reaction chambers 70, the lyophilized reagents can be easily solved. For example, the filler may be one filler selected from the group consisting of bovine serum albumin (BSA), polyethylene glycol (PEG), dextran, mannitol, polyalcohol, myo-inositol, citric acid, ethylene diamine tetra acetic acid disodium salt (EDTA2Na), and polyoxyethylene glycol dodecyl ether (BRIJ-35). One or more fillers may be selected from the fillers according to the types of reagents. For example, the surfactant may be one surfactant selected from the group consisting of polyoxyethylene, lauryl ether, octoxynol, polyethylene alkyl alcohol, nonylphenol polyethylene glycol ether; ethylene oxid, ethoxylated tridecyl alcohol, polyoxyethylene nonylphenyl ether phosphate sodium salt, and sodium dodecyl sulfate. One or more surfactants may be selected from the surfactants according to the types of reagents.

A checking chamber 71 may be provided to whether a sample dilution buffer is provided into the plurality of reaction chambers 70. Reagents are not accommodated in the checking chamber 71. The checking chamber 71 is disposed on an end of the channel 61. The reaction chambers 70 that are closest to an outlet of the dilution chamber 60 are first filled with the sample dilution buffer and the checking chamber 71 is last filled with the sample dilution buffer. Thus, when it is checked whether the checking chamber 71 is filled with a sample dilution buffer, it can be known whether all of the reaction chambers 70 are filled with the sample dilution buffer.

A reference unit 103 to which a sample is not supplied by the sample chambers 10a and 10b may be disposed on the platform 100. A dilution buffer may be stored in the dilution chamber 610 so as to obtain a standard value during reaction detection. Chambers 620 which are used to obtain detection standard values may be disposed outside the dilution chamber 610. Chambers 620 may be empty or may be filled with distilled water.

Although not shown, an air vent for discharging air filled in the microfluidic device may be disposed in the microfluidic device.

Figure 4:
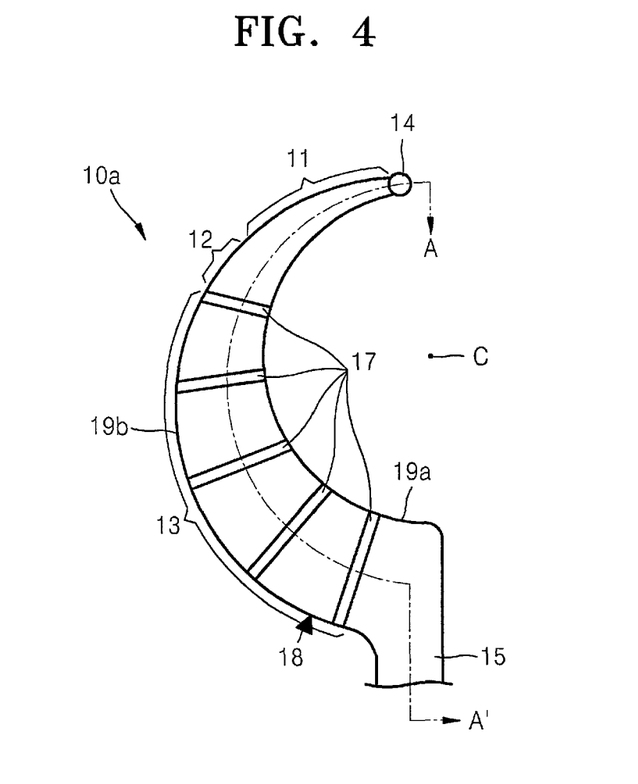
FIG. 4 is a detailed view of a sample chamber illustrated in FIG. 1, according to an embodiment.
Figure 5:
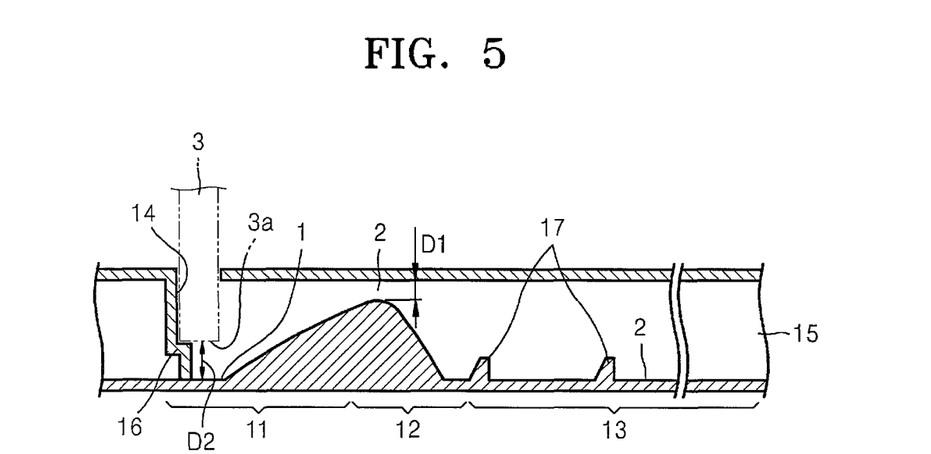
FIG. 5 is a cross-sectional view of the sample chamber 10a taken along line A-A' of FIG. 4, according to an embodiment.

FIG. 4 is a detailed view of the sample chamber 10a illustrated in FIG. 1, according to an embodiment. FIG. 5 is a cross-sectional view of the sample chamber 10a taken along a line A-A' of FIG. 4, according to an embodiment. Referring to FIGS. 4 and 5, the sample chamber 10a according to the current embodiment includes an introduction portion 11, a neck portion 12, and an accommodation portion 13.

Figure 6:
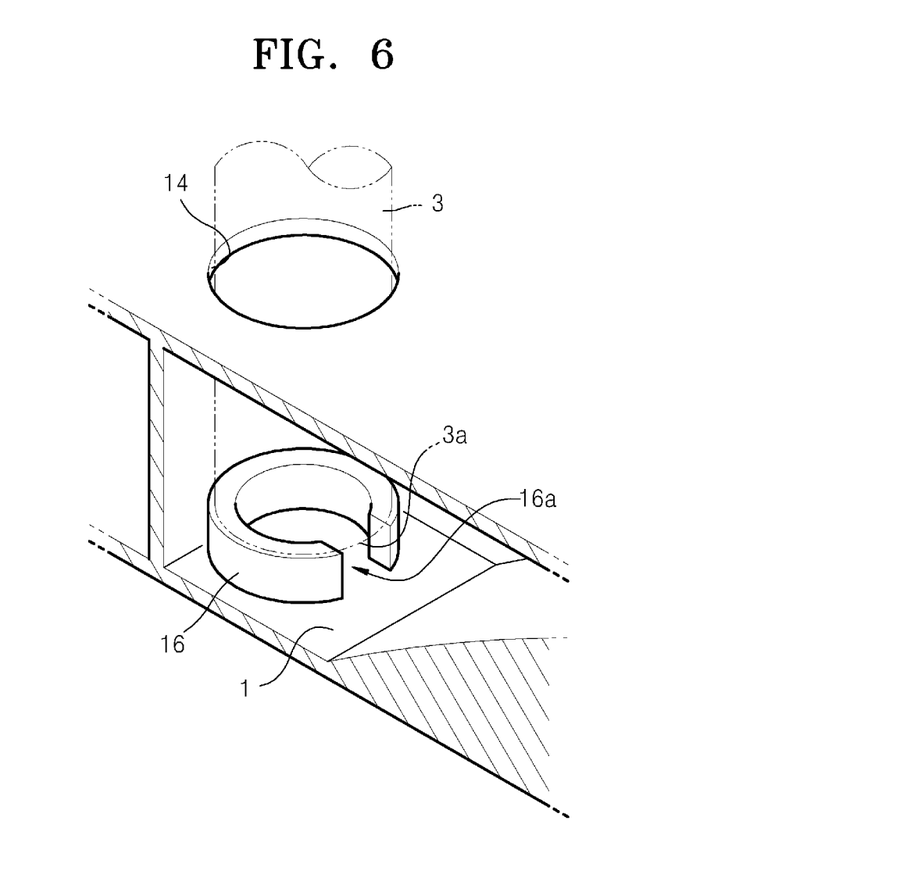
FIG. 6 is a perspective view of a distance maintaining portion according to an embodiment.

A loading hole 14 for loading a sample is disposed at the introduction portion 11. A syringe-type injector, such as a pipette or an injector having a different shape may be used as a sample loader 3. The size and shape of the loading hole 14 may be determined in accordance with the size and shape of a tip of the sample loader 3 so that the sample is prevented from flowing out of the loading hole 14 due to a sample loading pressure and from leaking to the outside while the sample is loaded. However, in this case, various types of sample loader 3 cannot be used. Thus, in the current embodiment, a distance maintaining portion 16 which maintains a distance D2 between a front end part 3a of the sample loader 3 inserted into the loading hole 14 and a bottom 1 of the introduction portion 11 is disposed in the introduction portion 11. As such, the sample does not leak through the loading hole 14 due to a sample loading pressure even if various types of sample loader 3 are used. The shape of the distance maintaining portion 16 is not limited to the example of FIG. 5. The distance maintaining portion 16 may have any shape maintaining the distance D2 between the front end part 3a of the sample loader 3 and the bottom 1 of the introduction portion 11. For example, as illustrated in FIG. 6, the distance maintaining portion 16 may protrude from the bottom 1 of the introduction portion 11 disposed below the loading hole 14, and an opening 16a is formed in the distance maintaining portion 16 toward the neck portion 12.

A discharge hole 15 is disposed in the accommodation portion 13. The discharge hole 15 is connected to the analysis unit 101, specifically, the sample measuring portion 30. Although not shown, the discharge hole 15 may form a capillary pressure so that the sample cannot move to the sample measuring portion 30 when a centrifugal force is not applied to the discharge hole 15, as will be described later. A valve which controls the flow of the sample may be disposed at the discharge hole 15. In addition, a sidewall 19a that is positioned to be distant from at least the center C, of two sidewalls 19a and 19b in a radial direction of the accommodation portion 13, may be formed so that a distance from the center C gradually increases toward the discharge hole 15 from the neck portion 12 so that the sample accommodated in the accommodation portion 13 can easily flow into the sample measuring portion 30 due to a centrifugal force.

The neck portion 12 forms a boundary between the introduction portion 11 and the accommodation portion 13 and provides a capillary pressure which is used to control the flow of the sample between the introduction portion 11 and the accommodation portion 13. In other words, the neck portion 12 is used to allow the sample to flow into the accommodation portion 13 from the introduction portion 11 due to a pressure of loading the sample through the loading hole 14 and to prevent the sample that reaches the accommodation portion 13 from flowing backward into the introduction portion 11.

To this end, the neck portion 12 has a depth D1 at which a capillary pressure can be formed. In other words, the neck portion 12 is a capillary valve which passes the sample only when a predetermined pressure is applied to the neck portion 12. As an example thereof, referring to FIG. 5, the bottom 1 of the introduction portion 11 may be inclined upward toward the neck portion 12. As such, the sample does not flow backward into the introduction portion 11 providing pressure exceeding a capillary pressure formed by the neck portion 12 is not applied to the sample accommodated in the accommodation portion 13.

Figure 7:
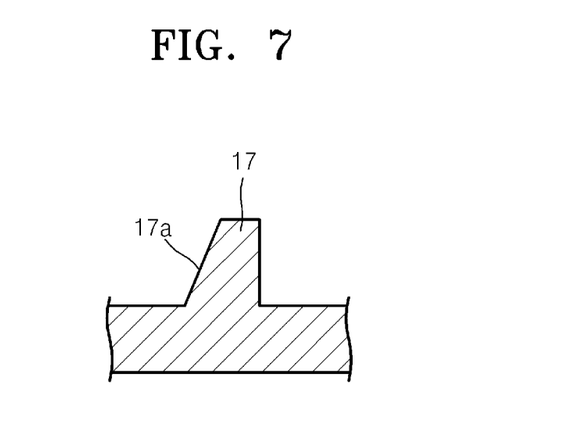
FIG. 7 is a cross-sectional view of a backward flow preventing portion according to an embodiment.

A backward flow prevention portion 17 may be disposed in the accommodation portion 13 and protrudes from a bottom 2 of the accommodation portion 13. For example, the backward flow prevention portion 17 may have a rib shape, as illustrated in FIG. 5. As an example thereof, as illustrated in FIG. 4, a plurality of backward flow prevention portions 17 may be disposed in a direction that crosses a direction of the sample flowing into the discharge hole 15 from the neck portion 12. The backward flow prevention portion 17 is used to apply a flow resistance to the sample so that the sample cannot easily flow back into the neck portion 12 from the accommodation portion 13. Referring to FIG. 7, an end part 17a of the backward flow prevention portion 17 facing the neck portion 12 may be inclined upward toward the discharge hole 15 so as to reduce resistance applied to the sample flowing into the discharge hole 15 within the accommodation portion 13. A marker 18 which checks whether the amount of the sample loaded is appropriate may be formed in the accommodation portion 13.

Figure 8:
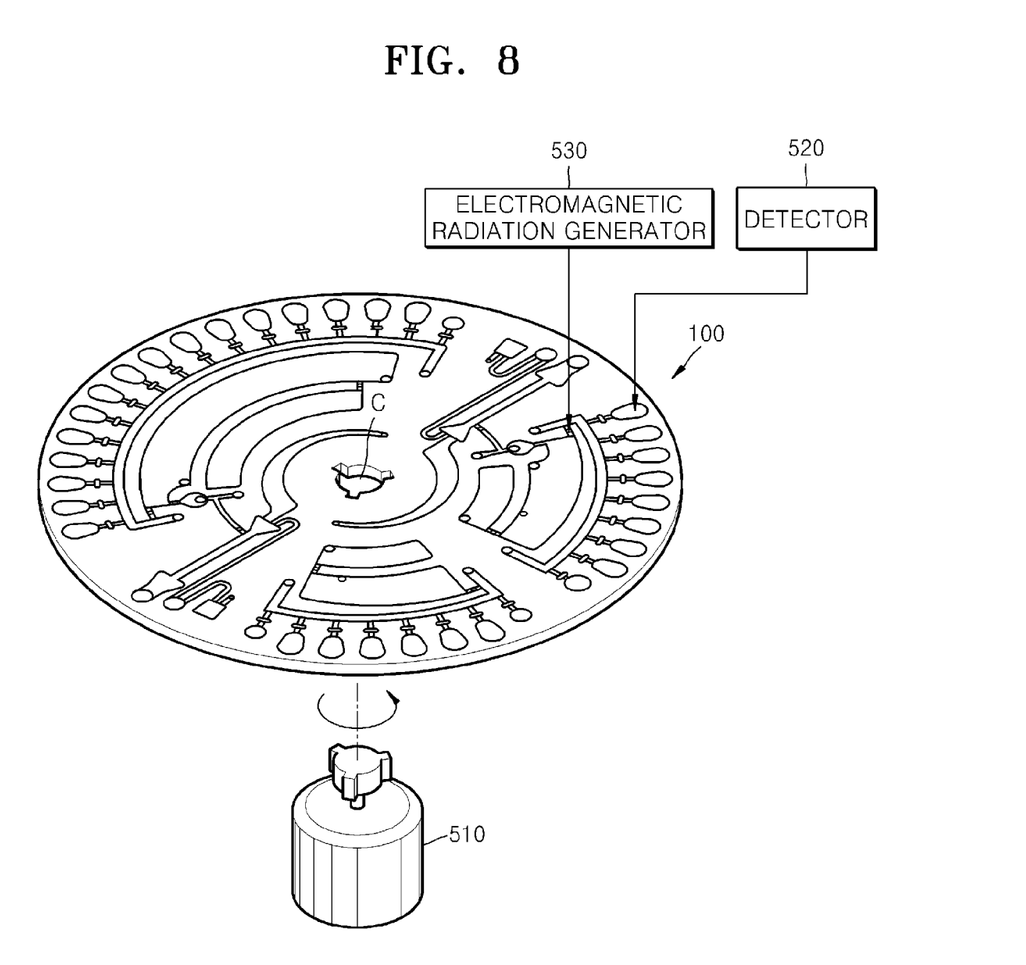
FIG. 8 schematically illustrates an analyzer using the microfluidic device of FIG. 1, according to an embodiment.

FIG. 8 schematically illustrates an analyzer using the microfluidic device of FIG. 1, according to an embodiment. Referring to FIG. 8, a rotation driving portion 510 rotates the microfluidic device so as to centrifugally separate a sample and to move a separated supernatant to a predetermined position of the microfluidic device. In addition, the rotation driving portion 510 stops the microfluidic device in a predetermined position so as to allow the reaction chambers 70 to face a photodetector 520. Although all of the elements of the rotation driving portion 510 are not shown, the rotation driving portion 510 may include a motor drive device which controls an angular position of the microfluidic device. For example, the motor drive device may use a step motor or a direct current (DC) motor. The photodetector 520 detects optical characteristics, such as fluorescence of material to be detected, emission characteristics and/or light absorption characteristics, for example. An electromagnetic wave generator 530 operates valves and radiates laser light, for example. The electromagnetic wave generator 530 may move in a radial direction of the microfluidic device.

Hereinafter, an operation of analyzing a sample by using the microfluidic device will be described. An operation of analyzing blood will be described in the current embodiment.

Blood taken from a person to be inspected is loaded into the sample chamber 10a by using the sample loader 3. In this case, since the distance D2 between the front end part 3a of the sample loader 3 and the bottom 1 of the introduction portion 11 is maintained by the distance maintaining portion 16, blood can be prevented from flowing backward due to a sample loading pressure and from leaking through the loading hole 11. Blood is delivered to the accommodation portion 13 via the neck portion 12 due to the sample loading pressure. An inspector checks the marker 18 disposed in the accommodation portion 13 with the naked eye to check whether an appropriate amount of blood is loaded into the sample chamber 10a.

A liquid dilution buffer, such as a buffer solution or distilled water is loaded into the dilution chamber 60. In this case, an appropriate amount of dilution buffer is loaded into the dilution chamber 60 so that the rate of dilution of a sample dilution buffer is appropriate to an inspection item.

The microfluidic device is mounted at the rotation driving portion 510 of the analyzer illustrated in FIG. 8. Blood accommodated in the accommodation portion 13 may be moved to the neck portion 12 while the microfluidic device is handled. However, blood cannot pass the neck portion 12 if pressure applied to the blood does not exceed a capillary pressure applied by the neck portion 12. In addition, since a resistance is applied to the flow of blood toward the neck portion 12 by the backward flow prevention portion 17, the pressure of blood applied toward the neck portion 12 can be reduced.

The rotation driving portion 510 rotates the microfluidic device at low speed continuously. Here, low speed is a rotation speed at which centrifugal separation does not occur in the sample measuring portion 30. Then, blood accommodated in the sample chamber 10a is moved to the sample measuring portion 30 due to centrifugal force and is filled in the sample measuring portion 30. When blood fully fills the sample measuring portion 30 and flows into the connection portion 42 of the channel 41, blood is flows to the sample detection chamber 40 through the channel 41. When the sample detection chamber 40 is fully filled with blood, blood is moved to the surplus sample chamber 20.

Then it is checked whether bloods exist in the sample detection chamber 40. For example, the rotation driving portion 510 may stop rotation of the microfluidic device and allow the sample detection chamber 40 to face the photodetector 520, so as to check whether blood exists in the sample detection chamber 40. In this regard, the photodetector 520 may radiate light on the sample detection chamber 40 and determine light absorption. Since the microfluidic device is transparent, the light absorption varies according to whether there is blood in the sample detection chamber 40. Thus, it can be checked whether blood exists in the sample detection chamber 40 by determining light absorption of the sample detection chamber 40.

When blood exists in the sample detection chamber 40, it means that an appropriate amount of blood for inspection is loaded into the sample chamber 10a and the sample measuring portion 30, and blood analysis can be performed. When blood does not exist in the sample detection chamber 40 even if the microfluidic device is rotated at low speed for sufficient time when blood is supplied to the sample measuring portion 30 from the sample chamber 10a, the amount of the sample loaded into the sample chamber 10a is not sufficient. Thus, the inspector can load blood into the sample chamber 10a, can rotate the microfluidic device at low speed and can check whether blood exists in the sample detection chamber 40.

The inspector can visually check whether blood exists in the sample detection chamber 40 before blood is loaded into the sample chamber 10a. In this case, when blood exists in the sample detection chamber 40, the microfluidic device has been already used for inspection. In this case, the inspector can replace the microfluidic device with a new microfluidic device. The previous checking operation may also be performed by mounting the microfluidic device on the rotation driving portion 510 of the analyzer and by measuring light absorption of the sample detection chamber 40 by using the photodetector 520.

When it is checked through the above-described operation that an appropriate amount of blood is accommodated in the microfluidic device, the rotation driving portion 510 rotates the microfluidic device at high speed. Here, high speed is a rotation speed at which centrifugal separation of blood occurs. Then, only a supernatant is collected in the supernatant collecting portion 311, and material having mass is collected in the sedimentation material collecting portion 312.

The rotation driving portion 510 is operated to allow the valve 313 to face the electromagnetic wave generator 530. When electromagnetic waves are irradiated on the valve 313, a valve material of the valve 313 is melted by electromagnetic wave energy, and the sample distribution channel 314 is opened. When the microfluidic device is rotated, the supernatant is moved to the measuring chamber 50 along the sample distribution channel 314 due to centrifugal force.

The rotation driving portion 510 is operated to allow the valve 51 to face the electromagnetic wave generator 530. When electromagnetic waves are irradiated on the valve 51, a valve material of the valve 51 is melted by electromagnetic wave energy, and the supernatant is flowed into the dilution chamber 60. In order to mix the supernatant and the dilution buffer, the rotation driving portion 510 may perform an operation of shaking the microfluidic device right and left several times. As such, a sample dilution buffer in which the supernatant and the dilution buffer are mixed is formed in the dilution chamber 60.

The rotation driving portion 510 is operated to allow the valve 62 to face the electromagnetic wave generator 530. When electromagnetic waves are irradiated on the valve 62, a valve material of the valve 62 is melted by electromagnetic wave energy, and the distribution channel 61 is opened. When the microfluidic device is rotated, the sample dilution buffer flows into the reaction chambers 70 and the checking chamber 71 through the distribution channel 61 due to centrifugal force. It can be checked that the sample dilution buffer flows into the checking chamber 71 by controlling the photodetector 520 to face the checking chamber 71 and by determining light absorption of the checking chamber 71.

The reagents accommodated in the reaction chambers 70 are mixed with the sample dilution buffer. In order to mix the reagents and the sample dilution buffer, the rotation driving portion 510 may perform an operation of shaking the microfluidic device right and left several times.

Then, the reaction chambers 70 face the photodetector 520 sequentially, and light is irradiated on a mixture of the reagents and the sample dilution buffer so that optical characteristics, such as fluorescence, emission characteristics and/or light absorption characteristics, can be determined. As such, it can be determined whether a predetermined material exists in the mixture or the amount of the predetermined material can be determined.

The case of blood analysis has been described above. However, the scope of one or more embodiments is not limited to this. As described above, the microfluidic device according to one or more embodiments can be used to perform analysis of various other extract materials that can be taken from the human body or living bodies and various extract materials that can be taken from the environment.

It should be understood that these exemplary embodiments described therein should be considered in a descriptive sense only and not for purposes of limitation. Descriptions of features or aspects within each embodiment should typically be considered as available for other similar features or aspects in other embodiments.

What is claimed is:
1. A microfluidic device comprising:
a sample chamber in which a sample is accommodated, wherein the sample chamber comprises:
an introduction portion comprising a loading hole through which the sample is loaded;
an accommodation portion comprising a discharge hole; and
a neck portion which forms a boundary between the introduction portion and the accommodation portion and provides a capillary pressure for controlling flow of the sample between the introduction portion and the accommodation portion,
wherein a bottom surface of the introduction portion is inclined upward to the neck portion from the loading hole to prevent flowing backward of the sample, and
wherein a distance from a center of the microfluidic device to a sidewall of the sample chamber gradually increases from the neck portion to the discharge hole.

2. The microfluidic device of claim 1, wherein the sample chamber further comprises a distance maintaining portion which maintains a distance between a front end part of a sample loader inserted in the loading hole and a bottom surface of the introduction portion, and the distance maintaining portion is disposed in the introduction portion.

3. The microfluidic device of claim 1, wherein the sample chamber further comprises a backward flow prevention portion which protrudes from a bottom surface of the accommodation portion.

4. The microfluidic device of claim 3, wherein the backward flow prevention portion is disposed in a direction that crosses a direction of a flow path of a sample flowing to the discharge hole.

5. The microfluidic device of claim 4, wherein an end part of the backward flow prevention portions is inclined upward toward the discharge hole.

6. The microfluidic device of claim 1, further comprising an analysis unit which is connected to the discharge hole of the accommodation portion, receives the sample accommodated in the sample chamber and analyzes the sample.

7. The microfluidic device of claim 6, wherein the analysis unit comprises:
a sample measuring portion which is connected to the sample chamber and measures the sample; and
a sample detection chamber which is connected to the sample measuring portion and in which a portion of the sample exceeding a capacity of the sample measuring portion is accommodated.

8. The microfluidic device of claim 7, wherein the analysis unit further comprises a surplus sample chamber which is connected to the sample detection chamber and in which a portion of the sample exceeding a capacity of the sample detection chamber is accommodated.

9. The microfluidic device of claim 7, wherein the sample measuring portion separates the sample into a supernatant and a sedimentation material by a centrifugal force.

10. The microfluidic device of claim 9, wherein the analysis unit further comprises:
a dilution chamber in which a dilution buffer is accommodated, which is connected to the sample measuring portion and to which the supernatant is supplied; and
a detection chamber in which a reagent is accommodated and to which a mixture of the supernatant and the dilution buffer is supplied from the dilution chamber.

11. The microfluidic device of claim 10, wherein the analysis unit further comprises a measuring chamber which is disposed between the dilution chamber and the sample measuring portion and accommodates a fixed amount of the supernatant.

12. The microfluidic device of claim 11, wherein the analysis unit further comprises a plurality of valves disposed in channels connecting the sample measuring portion, the measuring chamber, the dilution chamber, and the detection chamber, to control a flow of a fluid.

13. A microfluidic device comprising:
   a sample chamber in which a sample is accommodated, wherein the sample chamber comprises an introduction portion comprising a loading hole through which the sample is loaded, and a neck portion which provides a capillary pressure for controlling flow of the sample between the introduction portion and the accommodation portion, wherein a bottom surface of the introduction portion is inclined upward to the neck portion from the loading hole to prevent flowing backward of the sample, and wherein a distance from a center of the microfluidic device to a sidewall of the sample chamber gradually increases from the neck portion to the discharge hole; and
   an analysis unit which receives and analyzes the sample from the sample chamber,
   wherein the analysis unit comprises:
   a sample measuring portion which measures the sample; and
   a sample detection chamber which is connected to the sample measuring portion and in which a portion of the sample exceeding a capacity of the sample measuring portion is accommodated; and
   a surplus sample chamber which is connected to the sample detection chamber and in which a portion of the sample exceeding a capacity of the sample detection chamber is accommodated.

14. The microfluidic device of claim 13, wherein the sample chamber further comprises an accommodation portion comprising a discharge hole, wherein the neck portion forms a boundary between the introduction portion and the accommodation portion.

15. The microfluidic device of claim 14, wherein the sample measuring portion separates the sample into a supernatant and a sedimentation material by a centrifugal force.

16. The microfluidic device of claim 15, wherein the analysis unit further comprises:
   a dilution chamber in which a dilution buffer is accommodated, which is connected to the sample measuring portion and to which the supernatant is supplied; and
   a detection chamber in which a reagent is accommodated and to which a mixture of the supernatant and the dilution buffer is supplied from the dilution chamber.

17. The microfluidic device of claim 16, wherein the analysis unit further comprises a measuring chamber which is disposed between the dilution chamber and the sample measuring portion and accommodates a fixed amount of the supernatant.

18. The microfluidic device of claim 17, wherein the analysis unit further comprises a plurality of valves disposed in channels connecting the sample measuring portion, the measuring chamber, the dilution chamber, and the detection chamber, to control a flow of a fluid.

19. A microfluidic device comprising: a sample chamber in which a sample is accommodated; and
   an analysis unit which receives the sample from the sample chamber and comprises at
   least one reaction chamber for analyzing the sample, wherein the sample chamber comprises: a loading hole through which the sample is loaded; a discharge hole which is connected to the analysis unit; and a neck portion comprising a capillary valve which is disposed between the loading hole and the discharge hole and passes the sample only when a predetermined pressure is applied to the sample, wherein the capillary valve comprises a protrusion formed by first and second inclined portions of a bottom surface of the sample chamber, and wherein a distance from the center of the microfluidic device to a sidewall of the sample chamber gradually increases from the neck portion to the discharge hole.

20. The microfluidic device according to claim 19, wherein the sample chamber further comprises at least one backward flow prevention portion which protrudes from the bottom surface of the sample chamber at a position between the capillary valve and the discharge hole, and provides a flow resistance to the sample to impede the sample from flowing back towards the loading hole.

* * * * *